United States Patent [19]

Trust et al.

[11] 4,244,953

[45] Jan. 13, 1981

[54] SUBSTITUTED 6-PHENYL-5,6,7,8-TETRAHYDRO-1,2,4-TRIAZOLO-[4,3-A]PYRIDINES

[75] Inventors: Ronald I. Trust, Monsey; Jay D. Albright, Nanuet, both of N.Y.

[73] Assignee: American Cyanamid Company, Stamford, Conn.

[21] Appl. No.: 87,907

[22] Filed: Oct. 24, 1979

[51] Int. Cl.³ .................. A61K 31/435; C07D 471/04
[52] U.S. Cl. ..................................... 424/256; 546/119
[58] Field of Search ......................... 546/119; 424/256

[56] References Cited

U.S. PATENT DOCUMENTS 3,597,423 8/1971 Wiedemann et al. ............... 546/119

*Primary Examiner*—Alan L. Rotman
*Assistant Examiner*—Robert C. Whittenbaugh
*Attorney, Agent, or Firm*—Edward A. Conroy, Jr.

[57] ABSTRACT

This disclosure describes novel substituted 6-phenyl-5,6,7,8-tetrahydro-1,2,4-triazolo[4,3-a]pyridines and their use as agents for treating anxiety.

16 Claims, No Drawings

SUBSTITUTED 6-PHENYL-5,6,7,8-TETRAHYDRO-1,2,4-TRIAZOLO-[4,3-A]PYRIDINES

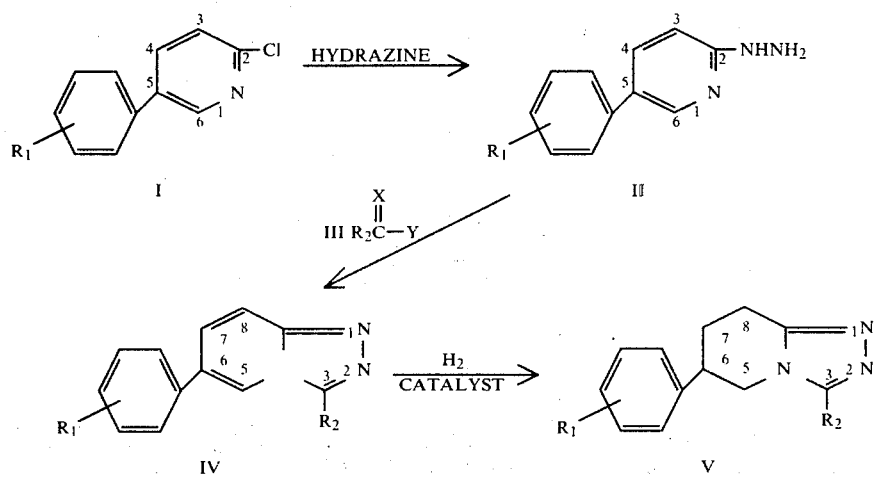

BRIEF SUMMARY OF THE INVENTION

This invention relates to new organic compounds and more particularly is concerned with novel substituted 6-phenyl-5,6,7,8-tetrahydro-1,2,4-triazolo[4,3-a]pyridines which may be represented by the following structural formula:

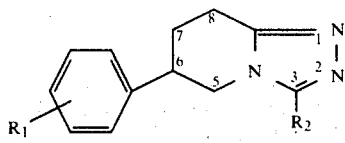

wherein $R_1$ is selected from the group comprising hydrogen, lower alkyl($C_1$-$C_4$), fluoro, chloro, bromo, trifluoromethyl, cyano, carboxyl, lower alkoxycarbonyl ($C_1$-$C_4$), carbamoyl, amino, acetamido, N,N-dialkylamino, with each alkyl group having up to 4 carbon atoms and the alkyl groups may be the same or different and lower alkoxy ($C_1$-$C_4$); $R_2$ is selected from the group comprising hydrogen and lower alkyl ($C_1$-$C_3$). The invention also includes novel compositions of matter containing the above-defined compounds useful as anxiolytic agents and the method of meliorating anxiety in mammals therewith.

DETAILED DESCRIPTION OF THE INVENTION

The novel compounds of the present invention are generally obtainable as white, tan, cream-colored or pale yellow crystalline solids having characteristic melting points and absorption spectra and which may be purified by recrystallization from common organic solvents such as methanol, ethanol, dimethylformamide, acetone, chloroform, ethyl acetate, methylene chloride, hexane, and the like, for mixtures of these. They are appreciably soluble in nonpolar organic solvents such as toluene and chloroform and the like, but are relatively insoluble in water.

The novel compounds of the present invention may be readily prepared in accordance with the following reaction schemes:

wherein $R_1$ and $R_2$ are as hereinabove defined, except $R_1$ may not be a group which would be altered under the conditions of catalytic hydrogenation, such as chloro, bromo and nitro. The groups X and Y in structure III are taken together to be that functionality which is capable of reacting with the terminal amino group in structure II to give cyclic products IV. Examples of those structural types of III are: a carboxylic acid (X=O; Y=OH); an acid chloride (X=O; Y=Cl); an amide [X=O; Y=NH_2, NHR_3 and NR_3R_4 where $R_3$ and $R_4$ are ($C_1$-$C_4$) alkyl groups]; an N,N-dialkylamide dialkylacetal where [X=(OR_5)_2; Y=NR_3R_4]; an ester (X=O; Y=OR_3) or an orthoester [X=(OR_5)_2; Y=OR_3]; or an anhydride

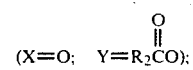

with the proviso that when $R_2$=H, then the reagents suitable are restricted to formic acid, lower alkyl orthoformates, lower alkyl formates, and dialkylformamides or their corresponding acetals and where $R_3$, $R_4$ and $R_5$ are lower alkyl ($C_1$-$C_4$). In accordance with the above reaction scheme, an appropriately substituted 5-phenyl-2-chloropyridine I is reacted with 95% hydrazine or hydrazine hydrate, which is preferably present in excess, at the reflux temperature in pyridine or lower alkanol solvent for a period of 12–48 hours to provide the corresponding substituted 2-hydrazino-5-phenyl-pyridine II. Treatment of II with one of the reagents III described above for a period of 1–24 hours at 50°–175° C. provides the corresponding substituted 6-phenyl-1,2,4-triazolo[4,3-a]pyridines IV. Reduction of IV with hydrogen in the presence of an appropriate catalyst such as palladium or platinum on carbon in an alcohol solvent with a small amount of base such as ammonia or potassium carbonate yields the substituted 6-phenyl-5,6,7,8-tetrahydro-1,2,4-triazolo[4,3-a]pyridines V of the present invention.

In those cases where the $R_1$ desired is unstable to hydrogenation conditions, the compounds may be prepared according to the following reaction scheme:

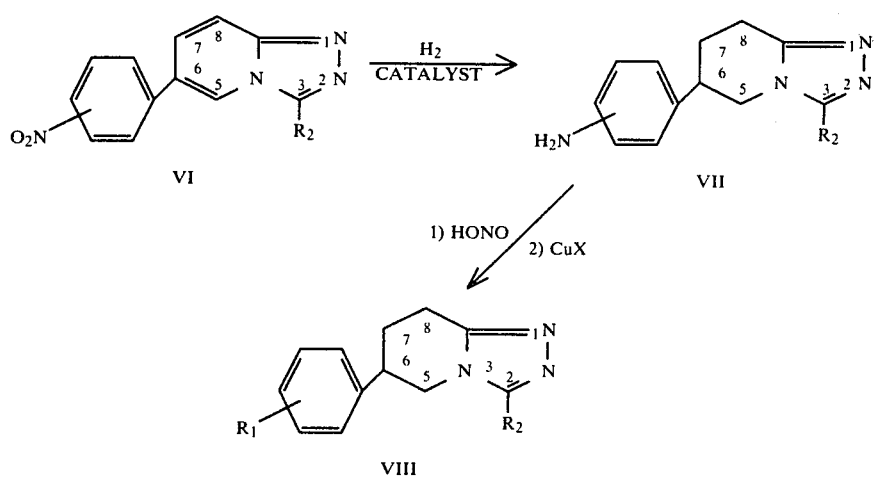

wherein $R_2$ is as hereinabove described. In accordance with the above scheme, a 6-(nitrophenyl)-1,2,4-triazolo[4,3-a]pyridine VI is reduced with hydrogen as described above to give the corresponding 6-(aminophenyl)-5,6,7,8-tetrahydro-1,2,4-triazolo[4,3-a]pyridine VII. Treatment of VII with a nitrosating agent, such as nitrous acid in the presence of a copper salt of a halide, such as chloride or bromide gives the 6-(halophenyl)-5,6,7,8-tetrahydro-1,2,4-triazolo[4,3-a]pyridines VIII of the present invention, where $R_1$ is halogen.

The starting materials IV for the compounds of the present invention may also be prepared in accordance with the following scheme:

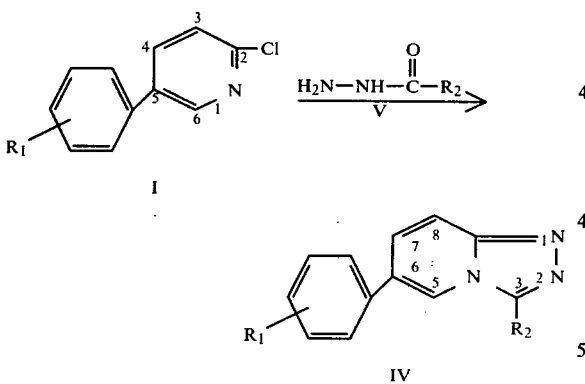

wherein $R_1$ and $R_2$ are as hereinabove defined. In accordance with the above reaction scheme, an appropriately substituted 2-chloro-5-phenylpyridine I is reacted with an acyl hydrazine of structure V in a lower alkanol or pyridine solvent at reflux temperature for a period of 12–48 hours to provide the corresponding 6-phenyl-1,2,4-triazolo[4,3-a]pyridines IV.

The appropriate 2-chloro-5-phenylpyridines I which are used as intermediates for the preparation of the compounds of the present invention may be prepared by any one of several convenient methods by one knowledgeable in the art. In particular, the 2-chloro-5-phenylpyridines I may be conveniently prepared by one of the following schemes:

First, the 2-chloro-5-phenylpyridine I, may be prepared by diazotization of 2-chloro-5-aminopyridine X in the presence of a phenyl derivative $R_1$—$C_6H_5$ IX according to J. Chem. Soc. 3181 (1949).

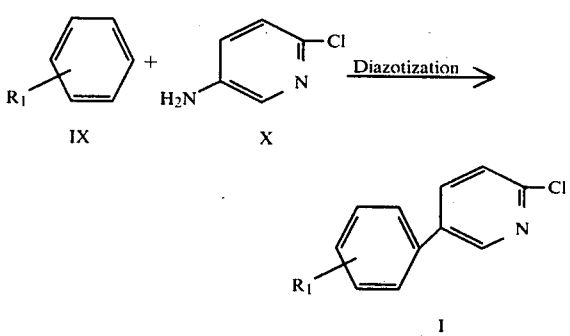

It is understood that in this reaction scheme it is preferable if $R_1$ is a group capable of rendering the phenyl ring sufficiently reactive to undergo attack by the diazotized 2-chloro-5-amino pyridine X. Such $R_1$ groups are those which are considered activating or weakly deactivating toward Friedel-Crafts alkylation, (according to G. Olah in *Friedel Crafts and Related Reactions,* Interscience, New York 1963). It is also understood that if the above scheme is employed and $R_1 \neq$ hydrogen in structure IX, then a mixture of isomeric products of structure I may be produced, with the $R_1$ moiety present in the 2' or 4' position of the benzene ring. However it is expected that an isomeric mixture of this type may be separable by any of a number of separation techniques familiar to those skilled in the art such as crystallization, distillation, sublimation, liquid chromatography or gas chromatography or the like.

Second, the 2-chloro-5-phenylpyridines I, may be preferably prepared in accordance with the following reaction scheme:

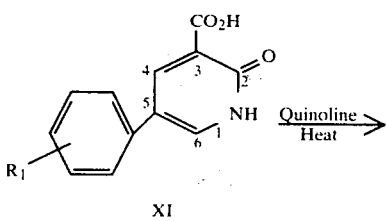

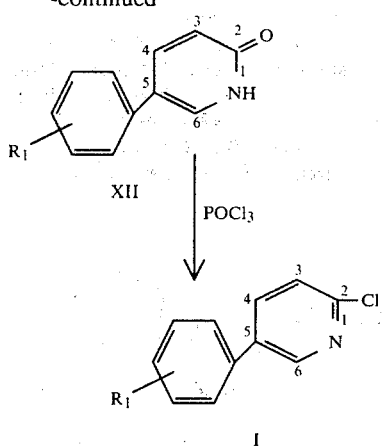

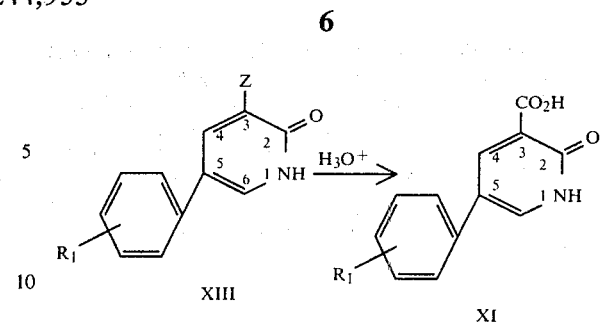

wherein $R_1$ is as hereinabove defined and Z is a group capable of being transformed into a carboxyl group by hydrolysis, such as cyano, alkoxycarbonyl or carbamoyl, thiocarbamoyl, or the like.

The compounds of formula XIII may be conveniently prepared according to the following scheme:

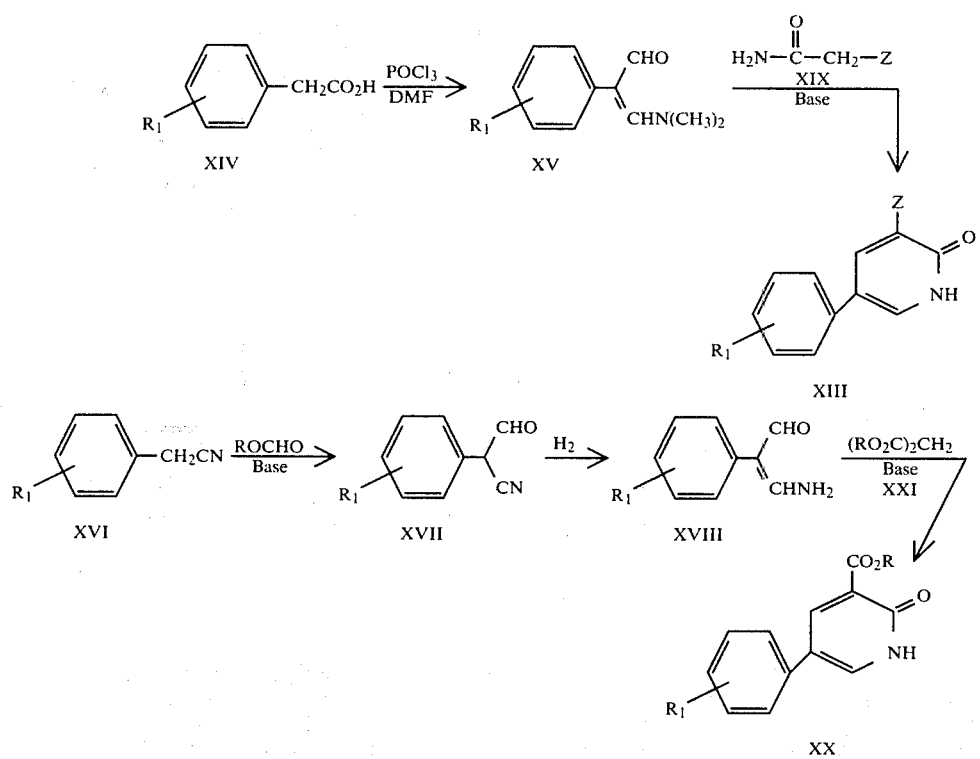

wherein $R_1$ is as hereinabove defined. In accordance with the above reaction scheme an appropriately substituted 1,2-dihydro-2-oxo-5-phenyl-3-pyridinecarboxylic acid XI is heated in quinoline at a temperature of 190°–235° C. for 4–24 hours in an inert atmosphere of either nitrogen, helium or argon to produce the appropriately substituted 5-phenyl-2(1H)-pyridinone XII. Treatment of XII with phosphorus oxychloride provides the substituted 2-chloro-5-phenylpyridine II.

The substituted 1,2-dihydro-2-oxo-5-phenyl-3-pyridinecarboxylic acids XI may be conveniently prepared by hydrolysis of a compound of the formula XIII, with an acid or a base such as sodium or potassium hydroxide.

wherein $R_1$ and Z are as hereinabove defined and R is a lower alkyl group ($C_1$–$C_4$). In accordance with the above scheme, the substituted 3-(dimethylamino)-2-phenyl-2-propenals XV may be condensed with an activated methylene compound of formula XIX with or without an alkali alkoxide catalyst such as sodium methoxide, sodium ethoxide or an organic base such as pyridine, piperidine or triethylamine to give the compounds of formula XIII. Examples of active methylene compounds of formula XIX may be cyanoacetamide, malonamide, methyl malonomate, ethyl malonomate, malonamic acid or 2-(N,N-dimethylthiocarbamoyl)acetamide. These same active methylene derivatives of formula XIX may be condensed with the substituted 3-amino-2-phenyl-2-propenals of structure XVIII in an identical fashion to produce the compounds of formula XIII. In addition, compounds XVIII may be condensed with dialkyl malonates XXI such as dimethyl malonate or diethyl malonate to yield specifically the lower alkyl 1,2-dihydro-2-oxo-5-phenyl-3-pyridinecarboxylates XX. The 3-(dimethylamino)-2-phenyl-2-propenals XV are conveniently prepared from an appropriately substituted phenylacetic acid XIV and dimethylformamide-phosphorus oxychloride. The 3-amino-2-phenyl-2-propenals XVIII are prepared from a substituted phenylacetonitrile by initial formylation with an alkyl formate and base followed by reduction with hydrogen using a Raney nickel catalyst. It is understood that while many of the 6-phenyl-5,6,7,8-tetrahydro-1,2,4-triazolo[4,3-a]pyridines of the present invention may be prepared by starting with either the substituted phenylacetic acids XIV or the phenylacetonitriles XVI with equal facility, it may sometimes be preferable to select that procedure which is most compatible with the chemical properties of the substituent $R_1$.

It is also understood that certain members of the substituted 6-phenyl-1,2,4-triazolo[4,3-a]pyridine, intermediates of this invention, may be preferably prepared from other substituted 6-phenyl-1,2,4-triazolo[4,3-a]pyridines, instead of starting with a unique starting material, as shown in the following schemes:

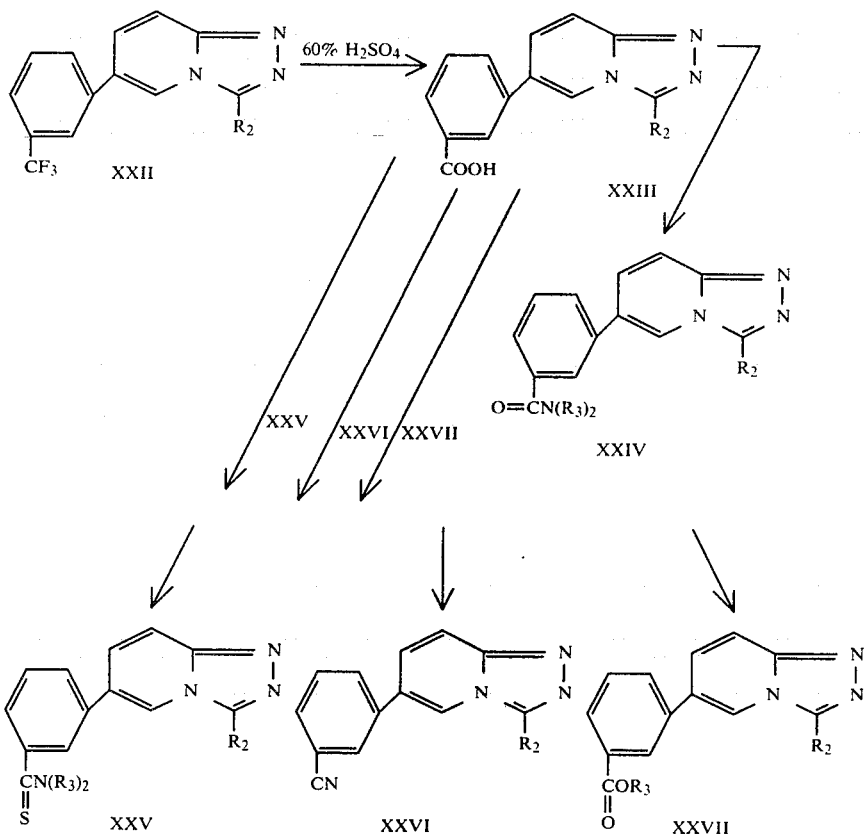

where $R_3$ is an alkyl group ($C_1$-$C_4$). In accordance with the above scheme, 3-methyl-6-[3-(trifluoromethyl)-phenyl]-1,2,4-triazolo[4,3-a]pyridine XXII ($R_2$=$CH_3$) may be hydrolyzed to the carboxylic acid XXIII which may be in turn converted to the derivatives XXIV-XXVII by standard methods. Also is noted the following transformations, which may be used to prepare other derivatives of this invention.

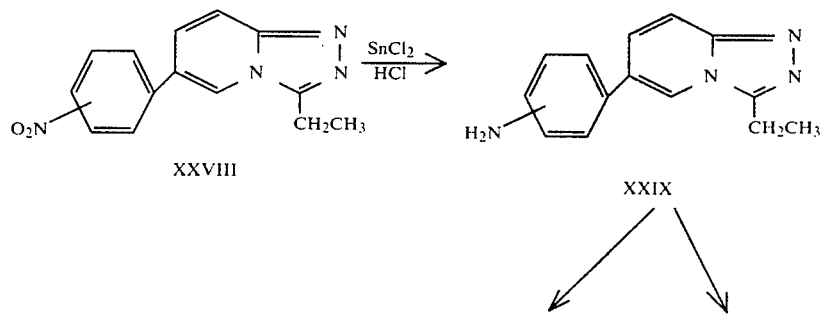

-continued

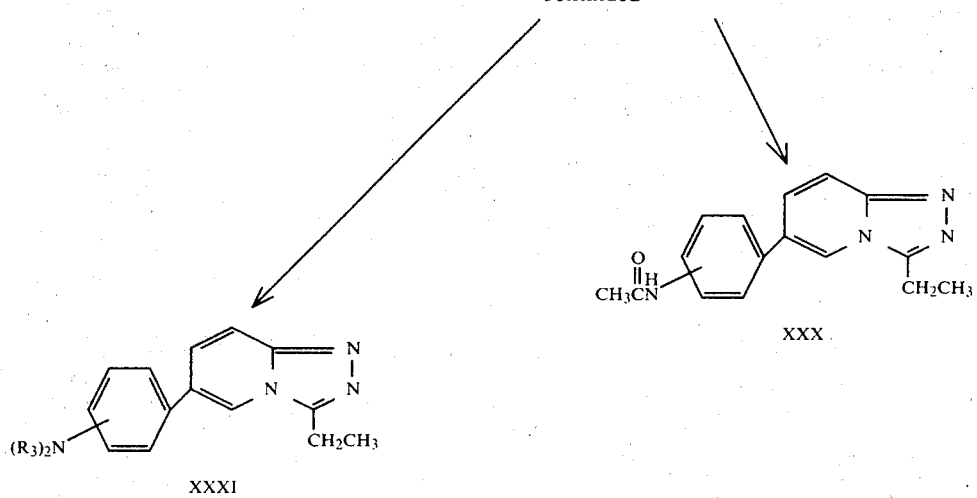

XXXI wherein R₃ is selected from an alkyl group of up to 4 carbon atoms and R₃ may be the same or different. In accordance with the above scheme, 3-ethyl-6-(4-nitrophenyl)-1,2,4-triazolo[4,3-a]pyridine XXVIII may be treated with an agent capable of reducing a nitro group to an amino, ie., stannous chloride in hydrochloric acid, to yield 3-ethyl-6-(4-aminophenyl)-1,2,4-triazolo[4,3-a]pyridine XXIX which may be transformed by standard methods to the derivatives XXX and XXXI.

The novel compounds of the present invention possess central nervous system activity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention have been shown to possess anxiolytic activity when tested as described above.

3-Methyl-6-phenyl-5,6,7,8-tetrahydro-1,2,4-triazolo[4,3-a]pyridine

3-Methyl-5,6,7,8-tetrahydro-6-[(3-trifluoromethyl)-phenyl]-1,2,4-triazolo[4,3-a]pyridine Another test used to measure anxiolytic activity comprises measurement of the ability of test compounds to inhibit the binding of ³H-diazepam to the brain receptors of warm-blooded animals. The test is described by R. F. Squires in Nature, 266, No. 21 page 732 (April 1977) and H. Mohler and T. Okada, Science, 198, 849 (1977). A modification of this test is used.

Diazepam Binding Assay

The animals used were male albino rats of the Wistar strain, weighing 150–200 g. each from Royalhart Farms. Diazepam (methyl-³H) was obtained from New England Nuclear. The test compounds were solubilized in either dimethylformamide, acetic acid, ethanol or hydrochloric acid.

Frontal cortex of rats was homogenized gently in 20 volumes of ice-cold 0.32 M. sucrose, centrifuged twice at 1000 g for 10 minutes and then recentrifuged at 30,000 g for 20 minutes to produce a crude P₂-synaptosomal fraction. The P₂-fraction was resuspended, twice the original volume, in hypotonic 50 nM. Tris·HCl (pH 7.4). The binding assay consisted of 300 μl. of the P₂-fraction suspension (0.350 mg.), 100 μl. of test drug and 100 μl. of 3H-diazepam (1.5 nM.), which was added to 1.5 ml. of 50 nM. Tris·HCl (pH 7.4). Non-specific binding controls and total binding controls received 100 μl. of diazepam (3 μm.) and 100 μl. of deionized water, respectively, in place of the test compound. Incubation for 20 minutes proceeded in ice and was terminated by filtration, under vacuum, through Whatman GF/C glass fiber filters. The filters were washed twice with 5 ml. of ice-cold 50 nM. Tris·HCl (pH 7.4) and placed in scintillation vials. After drying at 50°–60° C. for 30 minutes, 10 ml. of Beckman Ready-Solve HP was added and the radioactivity determined in a Beckman Scintillation Counter.

The percentage of inhibition of diazepam binding is calculated for each compound. A compound which exhibits the ability to inhibit binding by ≧20% is considered to be active.

Representative compounds of the present invention which are active when tested by the diazepam binding assay are listed below:

3-Methyl-6-phenyl-5,6,7,8-tetrahydro-1,2,4-triazolo[4,3-a]pyridine

3-Methyl-5,6,7,8-tetrahydro-6-[3-(trifluoromethyl)-phenyl]-1,2,4-triazolo[4,3-a]pyridine Another test which can be used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200–240 g. each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 or 60 minutes each rat was placed in individual black plexiglass chambers. A 10% dextrose solution was available ad libitum from a tap located in the rear of the chamber. A 0.3 milliampere constant current 60 Hz pulsed DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the shocks received by the test group are significantly different from the control group by the Mann-Witney U test.

The novel compounds of the present invention have been found to be highly useful for meliorating anxiety in mammals when administered in amounts ranging from about 0.1 mg. to about 20.0 mg./kg. of body weight per day. A preferred dosage regimen for optimum results would be from about 0.5 mg. to about 10.0 mg./kg. of body weight per day. Such dosage units are employed that a total of from about 35 to about 700 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-$\alpha$-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For instramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin, excipients such as dicalcium phosphate; a disintegrating agent such as corn starch, potato starch alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or organe flavor. Of course, any material used in preparing any dosage unit form should be pharmaceutically pure and substantially non-toxic in the amounts employed.

SPECIFIC DISCLOSURE

The following specific examples illustrate the preparation of the compounds of the present invention.

EXAMPLE 1

3-Methyl-5,6,7,8-tetrahydro-6-[3-(trifluoro methyl)phenyl]-1,2,4-triazolo[4,3-a]pyridine To a slurry of Vilsmeier reagent, prepared from 252 ml. of phosphorus oxychloride and 219 g. of N,N-dimethylformamide kept below 10° C. is added 123 g. of m-trifluoromethylphenylacetic acid. The mixture is stirred at ambient temperature for 30 minutes and then heated to 70°–80° C. during which time the mixture becomes effervescent. The mixture is kept at 70°–80° C. for 5.5 hours, allowed to cool to room temperature and then poured onto a sufficient quantity of ice (also added intermittently) so as to keep the mixture below 15° C. The mixture is then made alkaline by the careful portionwise addition of potassium carbonate (ice added intermittently to keep temperature >15° C.). When pH 10 is achieved, 500 ml. of toluene is added, and the mixture is heated on a steam bath for one hour. The layers are separated and the aqueous layer is extracted with an additional 500 ml. of toluene. The combined organic layers are washed well with water and dried over sodium sulfate. Evaporation of the solvent at reduced pressure yields 89.5 g. of 3-(dimethylamino)-2-[(3-trifluoromethyl)phenyl]-2-propenal, m.p. 128.5°–131.5° C.

To a solution of 36.7 g. of sodium methoxide in 650 ml. of methanol is added 28.2 g. of cyanoacetamide, followed by 71.5 g. of 3-(dimethylamino)-2-[(3-trifluoromethyl)phenyl]-2-propenal. The mixture is heated at reflux temperature for 16 hours during which time a yellow solid is separated. The mixture is concentrated at reduced pressure and water and acetic acid are added. The mixture is filtered and the resulting solid is washed with water and ethanol to give 61.8 g. of 1,2-dihydro-2-oxo-5-[3-(trifluoromethyl)phenyl]-3-pyridinecarbonitrile as colorless crystals, m.p. 242°–246° C.

A mixture of 1.32 g. of the above compound and a 1:1 mixture of concentrated hydrochloric acid and glacial acetic acid is heated at reflux temperature for 16 hours. A white solid is separated which is filtered, washed with water and dried to give 1.05 g. of 1,2-dihydro-2-oxo-5-[3-(trifluoromethyl)phenyl]-3-pyridinecarboxylic acid as a white solid, m.p. 295°–298° C. (dec.).

A mixture of 12.45 g. of the preceding compound and 40 ml. of quinoline is maintained at 225° C. for 16 hours under argon. The mixture is cooled and poured into hexane with chilling to give a tan solid which is taken up in methylene chloride, treated with charcoal, and diluted with hexane to give 6.45 g. of 5-[3-(trifluoromethyl)-2(1H)-pyridinone as a cream colored solid, m.p. 171°–176.5° C.

A mixture of 29.35 g. of 5-[3-(trifluoromethyl)-phenyl]-2(1H)-pyridinone and 120 ml. of phosphorus oxychloride is heated at reflux temperature for 16 hours, cooled and concentrated. The mixture is taken up in methylene chloride and poured onto ice-water. When the ice melts, the mixture is filtered and the layers are separated. The organic layer is washed with water then with saturated sodium bicarbonate and dried over sodium sulfate. Evaporation of the solvent at reduced pressure yields a solid which is recrystallized from hexane to give 28.3 g. of 2-chloro-5-[3-(trifluoromethyl)-phenyl]pyridine as pale yellow crystals, m.p. 40°–42° C.

A mixture of 15.5 g. of the preceding compound and 6 g. of 95% hydrazine in 75 ml. of dry pyridine is heated at reflux temperature for 16 hours, cooled and poured into ice-water. A tan solid is separated which is filtered, washed with water and dried to give 3.95 g. of 2-hydrazino-5-[3-(trifluoromethyl)phenyl]pyridine as a tan solid, m.p. 84°–87° C.

A mixture of 1.15 g. of the above compound and 15 ml. of ethyl orthoacetate is heated at reflux temperature for 4 hours. On cooling, a greenish crystalline solid is separated which is recrystallized from methylene chloride-hexane to give 0.5 g. of 3-methyl-6-[3-(trifluoromethyl)phenyl]-1,2,4-triazolo[4,3-a]pyridine as yellow green crystals, m.p. 185°–187° C.

To a solution of 922 mg. of the preceding compound and 6 ml. of concentrated ammonium hydroxide in 130 ml. of ethanol is added 200 mg. of 10% palladium on carbon. The mixture is shaken in a Parr apparatus in a hydrogen atmosphere (40 psi) until the uptake of hydrogen ceases. The mixture is filtered through diatomaceous earth, and the filtrate is concentrated to give a white solid which is recrystallized from methylene chloride-hexane to give 807 mg. of 3-methyl-5,6,7,8-tetrahydro-6-[3-(trifluoromethyl)]-1,2,4-triazolo[4,3-a]pyridine as white crystals, m.p. 150°–152° C.

EXAMPLE 2

5,6,7,8-Tetrahydro-6-[3-(trifluoromethyl)phenyl]-1,2,4-triazolo[4,3-a]pyridine

In a manner similar to Example 1, 3.25 g. of 2-hydrazino-5-[3-(trifluoromethyl)phenyl]pyridine is treated with 30 ml. of ethyl orthoformate to give 6-[3-(trifluoromethyl)phenyl]-1,2,4-triazolo[4,3-a]pyridine, m.p. 215°–218° C. which is hydrogenated to give the product of the Example.

EXAMPLE 3

3-Methyl-6-phenyl-5,6,7,8-tetrahydro-1,2,4-triazolo[4,3-a]pyridine

In a manner similar to Example 1, 91.12 g. of phenylacetic acid is treated with Vilsmeier reagent prepared from 280.5 ml. of phosphorus oxychloride and 268 g. of N,N-dimethylformamide to yield a yellow solid which is recrystallized from hexane to give 45 g. of 3-(dimethylamino)-2-phenyl-2-propenal, as a yellow solid, m.p. 48°–51° C.

To a solution of 28.5 g. of sodium methoxide in 500 ml. of methanol is added 22.2 g. of cyanoacetamide, followed by 42 g. of 3-(dimethylamino)-2-phenyl-2-propenal. The mixture is heated at reflux temperature for 16 hours during which time a yellow solid is separated. Water and acetic acid are added. The mixture is filtered and the resulting solid is washed with water and recrystallized from ethanol to give 12.5 g. of 1,2-dihydro-2-oxo-5-phenyl-3-pyridinecarbonitrile as an amorphous yellow solid.

A solution of 12.5 g. of the preceding compound in 100 ml. of 65% sulfuric acid is heated at reflux temperature for 4 hours. On cooling, yellow crystals separated. The mixture is poured into water, and the crude product is isolated by filtration and washing with water. The product is dissolved in 5% aqueous sodium hydroxide, filtered through diatomaceous earth and the filtrate is reacidified with hydrochloric acid. A white solid is formed which is filtered, washed with water and dried to give 10.9 g. of 1,2-dihydro-2-oxo-5-phenyl-3-pyridinecarboxylic acid, m.p. 296° C. (dec.).

A solution of 12.4 g. of the above acid and 50 ml. of quinoline is heated under argon at 215° C. for 6 hours. The mixture is cooled and hexane is added causing a gray solid to separate. The solid is recrystallized from chloroform-hexane after treatment with activated charcoal to afford 8.82 g. of 5-phenyl-2(1H)-pyridinone, m.p. 173°–177° C.

A mixture of the above 5-phenyl-2(1H)-pyridinone and 30 ml. of phosphorus oxychloride is heated at reflux temperature for 16 hours, cooled, and poured onto ice-water, causing a gray solid to separate. Chloroform is added and the mixture is filtered. The organic layer is washed with water, saturated sodium bicarbonate, brine solution and dried. Evaporation of the solvent provides an oil which is filtered through a pad of hydrous magnesium silicate. Hexane is added to the filtrate to precipitate a yellow solid identified as 2-chloro-5-phenyl pyridine. The product is treated with 4.5 ml. of 95% hydrazine in 75 ml. of pyridine at reflux for 40 hours, cooled and poured onto ice-water and filtered to remove the crude 2-hydrazino-5-phenylpyridine as a brown solid.

A solution of 0.85 g. of the above hydrazinopyridine in 10 ml. of ethyl orthoacetate is heated at reflux for 5 hours. On cooling pale yellow plates are separated which are washed with hexane to give 0.55 g. of 3-methyl-5-phenyl-1,2,4-triazolo[4,3-a]pyridine, m.p. 182°–184° C.

In a manner similar to that described in Example 1, the above product is hydrogenated to afford the product of the Example, m.p. 180°–182.5° C.

EXAMPLE 4

6-Phenyl-5,6,7,8-tetrahydro-1,2,4-triazolo[4,3-a]pyridine

In a manner similar to Example 3, 0.44 g. of 2-hydrazino-5-phenylpyridine is heated in 12 ml. of ethyl orthoformate to give 0.67 g. of 6-phenyl-1,2,4-triazolo[4,3-a]pyridine, as a tan solid, m.p. 181°–183.5° C. This product is hydrogenated to give the product of the Example, m.p. 144°–147° C.

EXAMPLE 5

6-(3-Fluorophenyl)-3-methyl-5,6,7,8-tetrahydro-1,2,4-triazolo[4,3-a]pyridine

In a manner similar to Example 1, 102.5 g. of m-fluorophenylacetic acid is treated with Vilsmeier reagent prepared from 306 g. of phosphorus oxychloride and 243 g. of dimethylformamide. The reaction mixture is reacted as described to give 90 g. of 3-(dimethylamino)-2-(3-fluorophenyl)-2-propenal as yellow crystals, m.p. 42°–43.5° C.

To a solution of 41.6 g. of sodium methoxide in 750 ml. of methanol is added 32.3 g. of cyanoacetamide followed by 74.2 g. of the aldehyde prepared above. The reaction mixture is heated at reflux temperature for 16 hours. Water and acetic acid are added, causing a cream-colored solid to separate. The product, 62.0 g. of 1,2-dihydro-5-(3-fluorophenyl)-2-oxo-3-pyridinecarbonitrile is isolated by filtration and washing with water and ethanol, m.p. 261°–266° C.

A solution of 59.6 g. of the preceding compound in 1500 ml. of 80% sulfuric acid is heated at reflux temperature for 6 hours, cooled to room temperature and poured onto ice. The fluffy gray solid that separates is filtered, washed well with water, and dried to give 51.65 g. of 1,2-dihydro-5-(3-fluorophenyl)-2-oxo-3-pyridinecarboxylic acid m.p. >300° C.

A mixture of 47.5 g. of the above compound and 100 ml. of quinoline is maintained at reflux temperature for 4 hours during which time the vigorous evolution of carbon dioxide is observed. The mixture is cooled and poured into hexane to give 17.15 g. of 5-(3-fluorophenyl)-2(1H)-pyridinone, m.p. 171°–176° C.

A mixture of 14.3 g. of the preceding compound and 60 ml. of phosphorus oxychloride is heated at reflux for 16 hours. The mixture is cooled and poured onto ice-water. The tan solid that is separated is filtered, washed with water and taken up in chloroform. The chloroform solution is then washed with water and dried. Evaporation of the solvent at reduced pressure affords 11 g. of 2-chloro-5-(3-fluorophenyl)pyridine as a tan solid. This solid is dissolved in 125 ml. of dry pyridine and 10.25 ml. of 95% hydrazine is added. The mixture is heated at reflux temperature for 16 hours, then cooled and poured into 2 liters of water. Filtration and washing with water yields 6 g. of 5-(3-fluorophenyl)-2-hydrazinopyridine as tan plates.

A mixture of 3 g. of the above hydrazinopyridine and 30 ml. of ethyl orthoacetate is heated at reflux for 4 hours and filtered to remove a tan solid which is washed with hexane to give 2.15 g. of 6-(3-fluorophenyl)-3-methyl-1,2,4-triazolo[4,3-a]pyridine, m.p. 179°–182° C. Reduction of this product as in Example 1 gives the product of the Example.

EXAMPLE 6

6-(3-Fluorophenyl)-5,6,7,8-tetrahydro-1,2,4-triazolo[4,3a]pyridine

In a manner similar to Example 5, 3 g. of 5-(3-fluorophenyl)-2-hydrazinopyridine and 30 ml. of ethyl orthoformate is heated at reflux temperature for 4 hours. On cooling, a tan solid is separated and is washed with hexane to give 2.25 g. of 6-(3-fluorophenyl)-1,2,4-triazolo[4,3-a]pyridine, m.p. 211°–215.5° C. Reduction of this product as in Example 5 provides the product of the Example.

EXAMPLE 7

Methyl 1,2-Dihydro-2-oxo-5-phenyl-3-pyridinecarboxylate

A solution of 21 g. of α-formylphenylacetonitrile [prepared according to G. Anderson, et al., J. Org. Chem., 7, 259 (1964)] in 250 ml. of ethanol is hydrogenated in a Parr apparatus in the presence of 4 teaspoonfuls of Raney nickel until the uptake of hydrogen ceases. The mixture is then filtered and washed with ethanol. Evaporation of the solvent yields a brown oil which is triturated with ether to give 7 g. of 3-amino-2-phenyl-2-propenal as a cream colored solid.

A mixture of 25.4 g. of this aldehyde and 27.32 g. of dimethyl malonate is added to a solution of 18.4 g. of sodium methoxide in 1 liter of methanol. The solution is stirred for 2 hours at room temperature and then heated at reflux temperature for 3 hours. The mixture is cooled and filtered to remove a mushy solid which is suspended in water and acidified with 10% hydrochloric acid to give a white solid which is filtered and washed with water and ethanol to give 18 g. of the product of the Example, m.p. 221°–224° C.

EXAMPLE 8

Methyl 1,2-Dihydro-5-(3-methoxy phenyl)-2-oxo-3-pyridinecarboxylate

In a manner similar to Example 7, m-methoxyphenylacetonitrile is treated with sodium methoxide and ethyl formate to afford α-formyl-(3-methoxyphenyl)acetonitrile. Hydrogenation of this product yields 3-amino-2-(3-methoxyphenyl)-2-propenal which is condensed with dimethyl malonate to afford the product of the Example.

EXAMPLE 9

6-(3-Methoxyphenyl)-3-methyl-5,6,7,8-tetrahydro-1,2,4-triazolo[4,3-a]pyridine Methyl 1,2-dihydro-5-(3-methoxyphenyl)-2-oxo-3-pyridinecarboxylate is treated with 1:1 hydrochloric acid-acetic acid to give 1,2-dihydro-5-(3-methyoxyphenyl)-2-oxo-3-pyridinecarboxylic acid. This product is boiled in quinoline to afford 5-(3-methoxyphenyl)-2(1H)-pyridinone as the product. Treatment of this product with phosphorus oxychloride provides 2-chloro-5-(3-methoxyphenyl)pyridine. The preceding product is treated with hydrazine to produce 2-hydrazino-5-(3-methoxyphenyl)pyridine. Treatment of this product with ethyl orthoacetate yields 6-(3-methoxyphenyl)-3-methyl-1,2,4-triazolo[4,3-a]pyridine. Hydrogenation of the above product gives the product of the Example.

EXAMPLE 10

6-(3-Methoxyphenyl)-5,6,7,8-tetrahydro-1,2,4-triazolo[4,3-a]pyridine

In a manner similar to Example 8, 2-hydrazino-5-(3-methoxyphenyl)pyridine is treated with ethyl orthoformate to give 6-(3-methoxyphenyl)-1,2,4-triazolo[4,3-a]pyridine. Hydrogenation of this product affords the product of the Example.

EXAMPLE 11

6-(4-Fluorophenyl)-3-methyl-5,6,7,8-tetrahydro-1,2,4-triazolo[4,3-a]pyridine In a manner similar to Example 1, p-fluorophenyl acetic acid is treated with Vilsmeier reagent to produce 3-(dimethylamino)-2-(4-fluorophenyl)-2-propenal. Treatment of this product with cyanoacetamide and sodium methoxide provides 1,2-dihydro-5-(4-fluorophenyl)-2-oxo-3-pyridinecarbonitrile. Hydrolysis of this product with acid gives 1,2-dihydro-5-(4-fluorophenyl)-2-oxo-3-pyridinecarboxylic acid. Treatment of this product with quinoline affords 5-(4-fluorophenyl)-2(1H)-pyridone, which is reacted with phosphorus oxychloride to give 2-chloro-5-(4-fluorophenyl)pyridine. Treatment of the above product with hydrazine produces 2-hydrazino-5-(4-fluorophenyl)pyridine. Treatment of this product with ethyl orthoacetate produces 6-(4-fluorophenyl)-3-methyl-1,2,4-triazolor[4,3-a]pyridine which yields the product of the Example on hydrogenation.

EXAMPLE 12

6-(4-Fluorophenyl)-5,6,7,8-tetrahydro-1,2,4-triazolo[4,3-a]pyridine

Treatment of 5-(4-fluorophenyl)-2-hydrazinopyridine with ethyl orthoformate produces 6-(4-fluorophenyl)-1,2,4-triazolo[4,3-a]pyridine. The preceding product is reduced by catalytic hydrogenation to give the product of the Example.

In a manner similar to the above examples may be prepared:
6-(2-Fluorophenyl)-3-methyl-5,6,7,8-tetrahydro-1,2,4-triazolo[4,3-a]pyridine
6-(2-Fluorophenyl)-5,6,7,8-tetrahydro-1,2,4-triazolo[4,3-a]pyridine
6-[(2-Trifluoromethyl)phenyl]-3-methyl-5,6,7,8-tetrahydro-1,2,4-triazolo[4,3-a]pyridine
6-[(2-Trifluoromethyl)phenyl]-5,6,7,8tetrahydro-1,2,4-triazolo[4,3-a]pyridine
6-(3-Methylphenyl)-3-methyl-5,6,7,8-tetrahydro-1,2,4-triazolo[4,3-a]pyridine
6-(3-Methylphenyl)-5,6,7,8-tetrahydro-1,2,4-triazolo[4,3-a]pyridine
6-(4-Methylphenyl)-3-methyl-5,6,7,8-tetrahydro-1,2,4-triazolo[4,3-a]pyridine
6-(4-Methylphenyl)-5,6,7,8-tetrahydro-1,2,4-triazolo[4,3-a]pyridine
6-(2-Methylphenyl)-3-methyl-5,6,7,8-tetrahydro-1,2,4-triazolo[4,3-a]pyridine
6-(2-Methylphenyl)-5,6,7,8-tetrahydro-1,2,4-triazolo[4,3-a]pyridine

EXAMPLE 13

3-Methyl-6-(4-nitrophenyl)-1,2,4-triazolo[4,3-a]pyridine p-Nitrophenylacetic acid is treated with Vilsmeier reagent to give 3-(dimethylamino)-2-(4-nitrophenyl)-2-propenal. This product is treated with cyanoacetamide and sodium methoxide to give 1,2-dihydro-5-(4-nitrophenyl)-2-oxo-3-pyridinecarbonitrile. The preceding product is hydrolyzed with 1:1 concentrated hydrochloric acid-acetic acid to give 1,2-dihydro-5-(4-nitrophenyl)-2-oxo-3-pyridinecarboxylic acid. The above product is boiled with quinoline to give 5-(4-nitrophenyl)-2(1H)-pyridone. When the preceding product is treated with phosphorus oxychloride, 2-chloro-5-(4-nitrophenyl)pyridine is obtained. This product is treated with hydrazine to give 2-hydrazino-5-(4-nitrophenyl)-pyridine. The above product is treated with ethyl orthoacetate to give the product of the Example.

In a similar manner may be prepared:
3-Methyl-6-(3-nitrophenyl)-1,2,4-triazolo[4,3-a]pyridine
3-Methyl-6-(2-nitrophenyl)-1,2,4-triazolo[4,3-a]pyridine

EXAMPLE 14

6-(4-Nitrophenyl)-1,2,4-triazolo[4,3-a]pyridine

2-Hydrazino-5-(4-nitrophenyl)pyridine is treated with ethyl orthoformate to give the product of the Example.

In a similar manner may be prepared:
6-(3-Nitrophenyl)-1,2,4-triazolo[4,3-a]pyridine
6(2-Nitrophenyl)-1,2,4-triazolo[4,3-a]pyridine

EXAMPLE 15

6-(4-Aminophenyl)-3-methyl-5,6,7,8-tetrahydro-1,2,4-triazolo[4,3-a]pyridine

3-Methyl-6-(4-nitrophenyl)-1,2,4-triazolo[4,3-a]pyridine is treated with hydrogen in the presence of palladium on carbon to give the product of the Example.

In a similar manner may be prepared:
6-(3Aminophenyl)-3-methyl-5,6,7,8-tetrahydro-1,2,4-triazolo[4,3-a]pyridine
6-(2-Aminophenyl)-3-methyl-5,6,7,8-tetrahydro-1,2,4-triazolo[4,3-a]pyridine

EXAMPLE 16

6-(4-Aminophenyl)-5,6,7,8-tetrahydro-1,2,4-triazolo[4,3-a]pyridine 6-(4-Nitrophenyl)-1,2,4-triazolo[4,3-a]pyridine is hydrogenated in the presence of palladium on carbond to give the product of the Example.

In a similar manner may be prepared:
6-(3-Aminophenyl)-5,6,7,8-tetrahydro-1,2,4-triazolo[4,3-a]pyridine 6-(2-Aminophenyl)-5,6,7,8-tetrahydro-1,2,4-triazolo[4,3-a]pyridine

EXAMPLE 17

6-(4-Chlorophenyl)-3-methyl-5,6,7,8-tetrahydro-1,2,4-triazolo[4,3-a]pyridine

3-Methyl-6-(4-aminophenyl)-5,6,7,8-tetrahydro-1,2,4-triazolo[4,3-a]pyridine is treated with nitrous acid in acidic medium and cuprous chloride is added to afford the product of the Example.
6-[(2-Trifluoromethyl)phenyl]-3-methyl-5,6,7,8-tetrahydro-1,2,4-triazolo[4,3-a]pyridine
6-[(2-Trifluoromethyl)phenyl]-5,6,7,8-tetrahydro-1,2,4-triazolo[4,3-a]pyridine
6-(3-Methylphenyl)-3-methyl-5,6,7,8-tetrahydro-1,2,4-triazolo[4,3-a]pyridine
6-(3-Methylphenyl)-5,6,7,8-tetrahydro-1,2,4-triazolo[4,3-a]pyridine
6-(4-Methylphenyl)-3-methyl-5,6,7,8-tetrahydro-1,2,4-triazolo[4,3-a]pyridine
6-(4-Methylphenyl)-5,6,7,8-tetrahydro-1,2,4-triazolo[4,3-a]pyridine
6-(2-Methylphenyl)-3-methyl-5,6,7,8-tetrahydro-1,2,4-triazolo[4,3-a]pyridine
6-(2-Methylphenyl)-5,6,7,8-tetrahydro-1,2,4-triazolo[4,3-a]pyridine

EXAMPLE 13

3-Methyl-6-(4-nitrophenyl)-1,2,4-triazolo[4,3-a]pyridine p-Nitrophenylacetic acid is treated with Vilsmeier reagent to give 3-(dimethylamino)-2-(4-nitrophenyl)-2-propenal. This product is treated with cyanoacetamide and sodium methoxide to give 1,2-dihydro-5-(4-nitrophenyl)-2-oxo-3-pyridinecarbonitrile. The preceding product is hydrolyzed with 1:1 concentrated hydrochloric acid-acetic acid to give 1,2-dihydro-5-(4-nitrophenyl)-2-oxo-3-pyridinecarboxylic acid. The above product is boiled with quinoline to give 5-(4-nitrophenyl)-2(1H)-pyridone. When the preceding product is treated with phosphorus oxychloride, 2-chloro-5-(4-nitrophenyl)pyridine is obtained. This product is treated with hydrazine to give 2-hydrazino-5-(4-nitrophenyl)-pyridine. The above product is treated with ethyl orthoacetate to give the product of the Example.

In a similar manner may be prepared:
3-Methyl-6-(3-nitrophenyl)-1,2,4-triazolo[4,3-a]pyridine
3-Methyl-6-(2-nitrophenyl)-1,2,4triazolo[4,3-a]pyridine

EXAMPLE 14

6-(4-Nitrophenyl)-1,2,4-triazolo[4,3-a]pyridine

2-Hydrazino-5-(4-nitrophenyl)pyridine is treated with ethyl orthoformate to give the product of the Example.

In a similar manner may be prepared:
6-(3-Nitrophenyl)-1,2,4-triazolo[4,3-a]pyridine
6-(2-Nitrophenyl)-1,2,4-triazolo[4,3-a]pyridine

EXAMPLE 15

6-(4-Aminophenyl)-3-methyl-5,6,7,8-tetrahydro-1,2,4-triazolo[4,3-a]pyridine

3-Methyl-6-(4-nitrophenyl)-1,2,4-triazolo[4,3-a]pyridine is treated with hydrogen in the presence of palladium on carbon to give the product of the Example.

In a similar manner may be prepared:
6-(3-Aminophenyl)-3-methyl-5,6,7,8-tetrahydro-1,2,4-triazolo[4,3-a]pyridine
6-(2-Aminophenyl)-3-methyl-5,6,7,8-tetrahydro-1,2,4-triazolo[4,3-a]pyridine

EXAMPLE 16

6-(4-Aminophenyl)-5,6,7,8-tetrahydro-1,2,4-triazolo[4,3-a]pyridine 6-(4-Nitrophenyl)-1,2,4-triazolo[4,3-a]pyridine is hydrogenated in the presence of palladium on carbon to give the product of the Example.

In a similar manner may be prepared:
6-(3-Aminophenyl)-5,6,7,8-tetrahydro-1,2,4-triazolo[4,3-a]pyridine
6-(2-Aminophenyl)-5,6,7,8-tetrahydro-1,2,4-triazolo[4,3-a]pyridine

EXAMPLE 17

6-(4-Chlorophenyl)-3-methyl-5,6,7,8-tetrahydro-1,2,4-triazolo[4,3-a]pyridine

3-Methyl-6-(4-aminophenyl)-5,6,7,8-tetrahydro-1,2,4-triazolo[4,3-a]pyridine is treated with nitrous acid in acidic medium and cuprous chloride is added to afford the product of the Example.

In a similar manner may be prepared:
6-(3-Chlorophenyl)-3-methyl-5,6,7,8-tetrahydro-1,2,4-triazolo[4,3-a]pyridine
6-(2-Chlorophenyl)-3-methyl-5,6,7,8-tetrahydro-1,2,4-triazolo[4,3-a]pyridine
6-(4-Chlorophenyl)-5,6,7,8-tetrahydro-1,2,4-triazolo[4,3-a]pyridine
6-(3-Chlorophenyl)-5,6,7,8-tetrahydro-1,2,4-triazolo[4,3-a]pyridine
6-(2-Chlorophenyl)-5,6,7,8-tetrahydro-1,2,4-triazolo[4,3-a]pyridine

We claim:

1. A compound selected from the group consisting of those of the formula

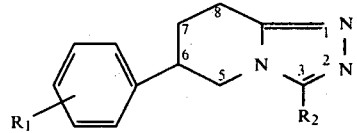

wherein $R_1$ is selected from the group consisting of hydrogen, lower alkyl ($C_1$–$C_4$), fluoro, chloro, bromo, trifluoromethyl, cyano, carboxyl, lower alkoxycarbonyl ($C_1$–$C_4$), carbamoyl, amino, acetamido, N,N-dialkylamino with each alkyl group having up to 4 carbon atoms and the alkyl groups being the same or different and lower alkoxy ($C_1$–$C_4$); $R_2$ is selected from the group comprising hydrogen and lower alkyl ($C_1$–$C_3$) and the pharmacologically acceptable acid-addition salts thereof.

2. The compound according to claim 1, 3-methyl-5,6,7,8-tetrahydro-6-[3-(trifluoromethyl)phenyl]-1,2,4-triazolo[4,3-a]pyridine.

3. The compound according to claim 1, 5,6,7,8-tetrahydro-6-[3-(trifluoromethyl)phenyl]-1,2,4-triazolo[4,3-a]pyridine.

4. The compound according to claim 1, 3-methyl-6-phenyl-5,6,7,8-tetrahydro-1,2,4-triazolo[4,3-a]pyridine.

5. The compound according to claim 1, 6-phenyl-5,6,7,8-tetrahydro-1,2,4-triazolo[4,3-a]pyridine.

6. The compound according to claim 1, 6-(3-fluorophenyl)-3-methyl-5,6,7,8-tetrahydro-1,2,4-triazolo[4,3-a]pyridine.

7. The compound according to claim 1, 6-(3-fluorophenyl)-5,6,7,8-tetrahydro-1,2,4-triazolo[4,3-a]pyridine.

8. The compound according to claim 1, 6-(3-methoxyphenyl)-3-methyl-5,6,7,8-tetrahydro-1,2,4-triazolo[4,3-a]pyridine.

9. The compound according to claim 1, 6-(3-methoxyphenyl)-5,6,7,8-tetrahydro-1,2,4-triazolo[4,3-a]pyridine.

10. The compound according to claim 1, 6-(4-fluorophenyl)-3-methyl-5,6,7,8-tetrahydro-1,2,4-triazolo[4,3-a]pyridine.

11. The compound according to claim 1, 6-(4-fluorophenyl)-5,6,7,8-tetrahydro-1,2,4-triazolo[4,3-a]pyridine.

12. The compound according to claim 1, 6-(4-aminophenyl)-3-methyl-5,6,7,8-tetrahydro-1,2,4-triazolo[4,3-a]pyridine.

13. The compound according to claim 1, 6-(4-aminophenyl)-5,6,7,8-tetrahydro-1,2,4-triazolo[4,3-a]pyridine.

14. The compound according to claim 1, 6-(4-chlorophenyl)-3-methyl-5,6,7,8-tetrahydro-1,2,4-triazolo[4,3-a]pyridine.

15. The method of meliorating anxiety in a mammal which comprises administering internally to said mammal an effective amount of a compound selected from the group consisting of those of the formula:

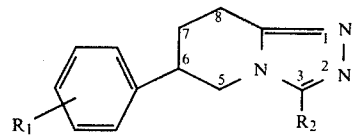

wherein $R_1$ is selected from the group consisting of hydrogen, lower alkyl ($C_1$-$C_4$), fluoro, chloro, bromo, trifluoromethyl, cyano, carboxyl, lower alkoxycarbonyl ($C_1$-$C_4$), carbamoyl, amino, acetamido, N,N-dialkylamino, with each alkyl group having up to 4 carbon atoms and the alkyl groups being the same or different, and lower alkoxy ($C_1$-$C_4$); $R_2$ is selected from the group comprising hydrogen and lower alkyl ($C_1$-$C_3$) and the pharmacologically acceptable acid-addition salts thereof.

16. The method according to claim 15 wherein the compounds are those of claims 2-14.

* * * * *